United States Patent [19]

Dawson et al.

[11] 4,151,199
[45] Apr. 24, 1979

[54] CYCLOPENTONE PROPANOIC ACID COMPOUNDS

[75] Inventors: William Dawson, Camberley; Michael J. Foulis, Bracknell; Norman J. A. Gutteridge, Owlsmoor, Nr. Camberley; Colin W. Smith, Bracknell, all of England

[73] Assignee: Lilly Industries Limited, London, England

[21] Appl. No.: 637,783

[22] Filed: Dec. 4, 1975

[51] Int. Cl.² .................. C07C 177/00; C07C 61/38
[52] U.S. Cl. .......................... 562/504; 260/448.8 R; 424/305; 424/317; 560/106; 560/122; 560/231
[58] Field of Search ....... 260/468 D, 514 D, 448.8 R, 260/448 R; 560/231, 122

[56] References Cited
U.S. PATENT DOCUMENTS 3,435,053  3/1969  Beal et al. ..................... 260/345.2

OTHER PUBLICATIONS

Hamberg et al., J. A. C. S. 91, 2177 (1909).
Miyano et al. J. O. C. 37, 1818 (1972).
Boot et al., Prostaglandins 8, 439 (1974).

Primary Examiner—Robert Gerstl
Attorney, Agent, or Firm—Kathleen R. S. Page; Everet F. Smith

[57] ABSTRACT

Propanoic acid derivatives of the formula:

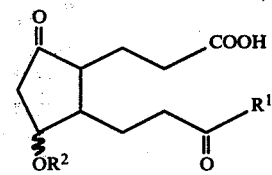

where $R^1$ is a $C_{1-8}$ alkyl group optionally substituted by hydroxyl or —COOH and $R^2$ is hydrogen or a protecting group, are useful as anti-thrombotic agents.

4 Claims, No Drawings

CYCLOPENTONE PROPANOIC ACID COMPOUNDS

This invention relates to a class of novel propanoic acid derivatives substituted in the three-position by a cyclopentenyl group and to a method of preparing such novel derivatives. The novel compounds of the invention possess useful pharmacological activity and, accordingly, the present invention also provides pharmaceutical compositions comprising one or more of said novel compounds.

In the specification of our U.S. application Ser. No. 637,782 filed Dec. 4, 1975 now U.S. Pat. No. 4,039,571, there is described the preparation of novel intermediates having the structure:

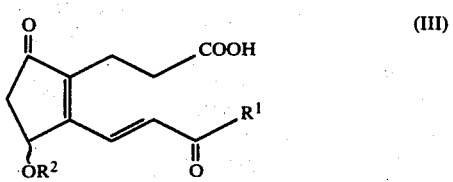

(III)

and salts and esters thereof, where $R^1$ is a straight or branched alkyl group having from 1 to 10 carbon atoms being optionally substituted by a hydroxyl or —COOH group, or is an optionally substituted phenyl group, and $R^2$ is hydrogen or a protecting group. As stated in said specification, the foregoing compounds may exist in racemic or optically active form.

It has now been discovered that the above intermediates of formula (III) can be catalytically reduced to provide a novel class of propanoic acid derivatives possessing useful and valuable pharmacological activity.

According to a first aspect of the present invention there is provided a compound of formula (II):

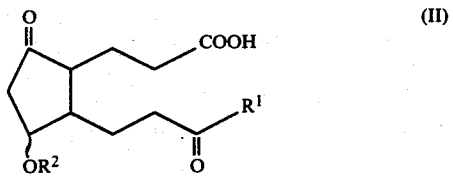

(II)

wherein $R^2$ is hydrogen or a protecting group for example an acyl, tetrahydropyranyl, trialkylsilyl, or aroyl, such as benzoyl, group; and $R^1$ is a straight or branched alkyl group having from 1 to 10 atoms being optionally substituted by a hydroxyl or COOH group, or is an optionally substituted phenyl or benzyl group; or a salt or ester thereof.

The compound of formula (II) may exist in racemic or optically active form. Referring to the stereo-relationship between the substituents on the 1 and 2, and 2 and 3 positions of the cyclopentane ring, the four possible racemic forms may be described as the trans/trans, trans/cis, cis/trans and cis/cis forms, each of which may be resolved into a pair of enantiomers represented by the following partial formulae showing the absolute configurations thereof:

| trans/trans | trans/cis | cis/trans | cis/cis |
|---|---|---|---|

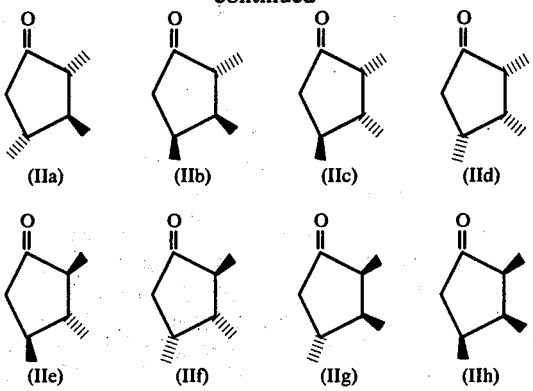

| (IIa) | (IIb) | (IIc) | (IId) |

| (IIe) | (IIf) | (IIg) | (IIh) |

Accordingly where, as in formula (II) above and in the formulae shown hereinafter, no specific stereochemistry is indicated, the structure shown or being described is intended to cover the mixture of the above racemates as well as the individual racemates and optical isomers described above.

The preferred compounds of formula (II) are those in which $R^1$ is a straight or branched $C_{1-8}$ alkyl group optionally substituted by a hydroxyl or COOH group and $R^2$ is hydrogen. Preferred protecting groups for $R^2$ are acetyl and trimethylsilyl. Most advantageously the compound of formula (II) is one with the configuration (IIb or IIh) or one of the above racemic mixtures in which $R^1$ is n-pentyl or 4-carboxybutyl.

The compounds of formula (II) have been found to possess useful anti-thrombotic activity coupled with low toxicity.

According to a second aspect of the present invention there is provided a method of preparing a compound of formula (II) or a salt or ester thereof, which comprises reducing a compound of formula (III):

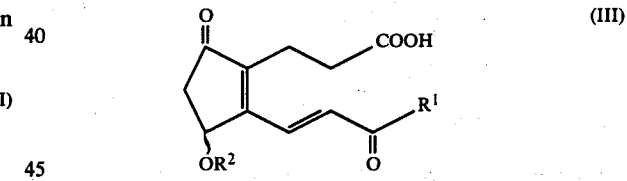

(III)

wherein $R^1$ and $R^2$ are as defined above, or a salt or ester thereof, followed by one or more of the following optional steps:

(a) where $R^2$ in the compound of formula (II) is a hydrogen atom, protecting the endocyclic hydroxyl group;

(b) salifying or esterifying a resultant free acid of formula (II);

(c) desalifying or deesterifying a resulting salt or ester of formula (II); and (d) where $R^2$ is a protecting group in the resultant compound of formula (II) removing said group in the resultant compound of formula (II) in which $R^2$ represents a hydrogen atom.

The reduction of (III) can be accomplished by catalytic hydrogenation using, for example, hydrogen under pressure, e.g. preferably in the range 40–60 p.s.i., over a group VIII metal, preferably palladium. Suitable solvents are alkanols, e.g. ethanol. Addition of triethylamine has been found to facilitate the process.

The above reduction is believed to proceed via an intermediate of formula:

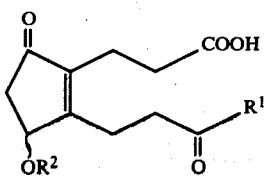

or a salt or ester thereof, where $R^1$ and $R^2$ are as defined above and accordingly, in a further aspect of the invention, there is provided a method of preparing a compound of formula (II) which comprises the catalytic reduction of a compound of formula (IV). Using mild reduction conditions at atmospheric pressure the compounds of formula (III) can be reduced selectively to the compounds of formula (IV). Hydrogen over palladium for example may be used.

Where $R^2$ is a bulky group such as trialkylsilyl, compounds of formula IV are more conveniently prepared using 10% palladium on charcoal at, for example, 50 p.s.i.

Alternatively, compounds of formula (II) can be prepared by reduction in the manner described above of a compound of formula (V):

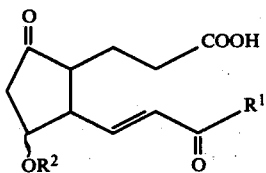

which in turn may be obtained by reaction of a compound of formula (VI), or a salt or ester thereof:

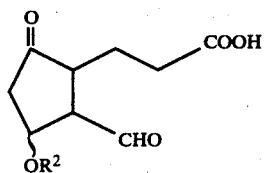

with a Wittig reagent of formula

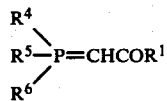

where $R^1$ is as above defined and wherein $R^4$, $R^5$ and $R^6$ are optionally substituted phenyl.

Similar reaction conditions to those employed in our copending application Ser. No. 637,782 filed Dec. 4, 1975 now U.S. Pat. No. 4,039,571, can be utilised to accomplish the above Wittig reaction.

The aldehydes of formula (VI) can be derived from the aldehydes of formula (VII), or salts or esters thereof,

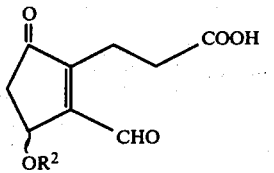

where $R^2$ is hydrogen, acyl or benzoyl, described in the specification of our copending application Ser. No. 459,829 filed Oct. 4, 1974, now U.S. Pat. No. 4,027,036 by reduction using, for example, palladium over hydrogen. Conveniently, the aldehyde is protected prior to reduction, for example, by formation of the corresponding hemi-acetal. The aldehydes of formula (VII) can also be reduced using Zn/aqueous/acid, e.g. acetic acid, using THF as a co-solvent. To prepare compounds of formula (VI) in which $R^2$ is a protecting group other than acyl or benzoyl, an aldehyde of formula (VII), where $R^2$ is hydrogen, can be reduced and the endocyclic hydroxyl group then reacted with an appropriate reagent.

The intermediates of formula (IV), (V) and (VI) are novel, as is the reduction of compounds of formula (V) to compounds of formula (II). Accordingly, each of these features is provided in further aspects of the invention.

Compounds of formula (II) can be labelled, i.e. one or more of the carbon, hydrogen or oxygen atoms may be in the form of one of their less common, even radioactive, isotopes. For example, one or more of the hydrogen atoms can be deuterium or tritium, or one or more of the carbon atoms may be $C^{13}$ or $C^{14}$ atoms. Such labelled compounds have value as diagnostic agents, for instance, in GCMS isotope dilution assays.

The labelled atom can be introduced into the compound of formula (II) or (III) at any stage in the synthesis. The methods by which the labelled atom can be introduced are well-known in the art, see for example, "Organic Syntheses with Isotopes" by A. Murray (III) and D. L. Williams, Parts I and II, published in 1958 by Interscience, New York and London.

The salts of the acids of formula (II) are preferably alkali metal salts such as the sodium or potassium salts, the preparation of which can be accomplished by reaction of the acid with an appropriate base such as an alkali metal hydroxide, carbonate or hydrogen carbonate. In addition, the salt may be an amine salt such as a tertiary amine salt, for example, that formed from triethylamine.

Examples of suitable esters of the acids of formula (II) include alkyl, silyl, cycloalkyl, cycloalkyl-alkyl, aralkyl, heteroaryl-alkyl, alkylaminoalkyl and alkoxyalkyl esters. Preferred esters are the $C_{1-4}$ alkyl esters optionally substituted by one or more halogen atoms such as the methyl, ethyl, n-propyl, isobutyl, t-butyl, chloromethyl, trifluoromethyl, 2-chloroethyl and 2,2,2-trichloroethyl esters. The preparation can be carried out in conventional manner, for example, by reacting the free acid of formula (II) with an appropriate alcohol in the presence of an acid catalyst. Thus, the preferred esters of the invention may be prepared by reaction with, for example, methanol, ethanol, isopropanol, t-butanol, chloromethanol or 2,2,2-trichloroethanol in the presence of p-toluene sulphonic acid. The $C_{1-4}$ alkyl esters of the invention may also be prepared by reaction of the free acid with a diazoalkane such as a diazomethane or diazoethane.

When $R^2$ in formula (II) above is an acyl or aroyl group such as benzoyl, the preferred examples of such groups are $C_{2-4}$ acyl, $C_{2-4}$-haloacyl, benzoyl, nitrobenzoyl, halobenzoyl, $C_{1-4}$ alkyl-benzoyl, and $C_{2-4}$ alkoxybenzoyl, and especially acetyl, propionyl, chloroacetyl, 3,3,3-trichloropropionyl, benzoyl, p-nitrobenzoyl, p-methylbenzoyl, p-chlorobenzoyl, and p-methoxybenzoyl. If $R^2$ is hydrogen in the starting material of formula (III) and hence the end product of formula (II), the latter may readily be converted to a compound of formula (II) in which $R^2$ is an acyl or aroyl group by reaction with an appropriate acylating or aroylating agent, for example, an acyl or benzoyl halide, or an acid anhydride such as acetic anhydride, propionic anhydride, 3,3,3-trichloropropionic anhydride, acetyl chloride, benzoyl chloride, p-chlorobenzoyl chloride or p-nitrobenzoyl chloride. The above acylation or aroylation is preferably carried out on the ester.

$R^2$ in the compounds of formula (II) may also be trialkylsilyl, preferably trimethylsilyl, group. Such compounds can be prepared by reacting a compound of formula (II), where $R^2$ is hydrogen, with, for example, chlorotrimethyl silane in the presence of 1,1,1-3,3,3-hexamethyldisilazane using an inert anhydrous solvent such as tetrahydrofuran. Such methods are well-known in the art, see for example, E. J. Corey, et al., *Journal of the American Chemical Society*, 94, 17, 6190-1. The trialkyl silyl group can be removed by hydrolysis.

As indicated above, the compounds of formula (II) are prepared in racemic or optically active form, depending on the form of the starting material of formula (III).

The racemates and enantiomorphs of formula (II) and their salts and esters, possess useful pharmacological activity, especially anti-thrombotic activity, and this property coupled with their low toxicity, renders them useful in the treatment of thrombosis in animals especially humans. This activity has been demonstrated at doses from about 1 to 150 mg./kg. depending on the test procedure used. In the treatment of humans, the effective dosage range will normally lie between 5 and 25 mg./kg. although other dosing schedules may be used at the discretion of the physician treating the patient.

In therapeutic use, the active compounds of the invention may be administered enterally, preferably orally, or parenterally, preferably intravenously, and for this purpose they will normally be formulated into pharmaceutical compositions comprising the active ingredient in association with at least one pharmaceutically acceptable carrier therefor. Such compositions form a part of this invention and will normally consist of the active ingredient mixed with a carrier or diluted by a carrier, or enclosed or encapsulated by a carrier, in the form of a capsule, sachet, cachet or other container. The carrier may be a solid, semi-solid or liquid material which serves as a vehicle, excipient, coating agent, or medium for the active ingredient. Some examples of the carriers which may be used are lactose, dextrose, sucrose, sorbitol, mannitol, starch, gum acacia, calcium phosphate, liquid paraffin, cocoa butter, oil of theobroma, alginates, tragacanth, gelatin, methylcellulose, polyoxyethylene sorbitan monolaurate, methyl- or propyl-hydroxybenzoate, ethyl cellulose acetate phthalate; low viscosity acetyl cellulose acetate, paraffin wax, mineral wax, vegetable wax, vegetable gum, silicone rubbers such as liquid polydimethylsiloxane rubber, plasticised or unplasticised polyvinyl chloride, plasticised polyethylene terephthalate, modified collagen, cross-linked hydrophilic polyether gel, cross-linked polyvinyl alcohol or cross-linked partially hydrolysed polyvinyl acetate.

Advantageously the compositions of the invention are formulated in a dosage unit form containing from 5 to 500 mg. (preferably 10-150 mg.) of the active ingredient. Examples of suitable dosage unit forms are tablets, hard or soft gelatin capsules, microcapsules and suppositories as well as drug dispensing systems comprising the active ingredient contained in a flexible, imperforate polymeric material through which the drug may be released slowly by diffusion. More generally, the term "dosage unit form" as used herein means a physically discrete unit containing the active ingredient, generally in admixture with and/or enclosed by a pharmaceutical carrier, the quantity of active ingredient being such that one or more units are normally required for a single therapeutic administration.

The following Examples illustrate the invention:

EXAMPLE 1

3-[3-Hydroxy-5-oxo-2-(3-oxo-octan-1-yl)cyclopent-1-enyl]propanoic acid

3-[3-Hydroxy-5-oxo-2-(3-oxo-oct-1-enyl)cyclopent-1-enyl]propanoic acid (1.0 g.) was dissolved in absolute ethanol (50 ml.) and triethylamine (5 ml.) and hydrogenated over a Raney Nickel W2 catalyst at room temperature for 80 minutes. The catalyst was removed by filtration and the filtrate rotary evaporated to a crystalline solid. The solid was dissolved in chloroform and shaken with 1 M hydrochloric acid and then with brine. After drying over anhydrous sodium sulphate the solvent was removed by rotary evaporation to yield an oil. Chromatography on a silicic acid column (Bio Sil A) with chloroform as eluant was effective in purification of the product, 3-[3-hydroxy-5-oxo-2-(3-oxo-octan-1-yl)cyclopent-1-enyl]propanoic acid.

Further purification may be achieved by shaking a chloroform solution of the product with sodium bicarbonate solution to give its sodium salt. The aqueous phase containing this salt was washed with chloroform and then acidified with 1 M hydrochloric to pH 2 and reextracted with chloroform. The chloroform extract was dried and rotary evaporated a light yellow oil which on trituration with cyclohexane yielded the pure product. The ultra-violet spectrum exhibited absorption at 235 nm (E 10,000). The mass spectrum gave a molecular ion at 382 units (methyl ester; trimethyl silyl ether) M.W. 382.

EXAMPLE 2

Hydrogenation of Trimethylsilyl-3-[5-oxo-2-(3-oxo-oct-1-enyl)-3-trimethylsilyloxy-cyclopent-1-enyl]propanoate

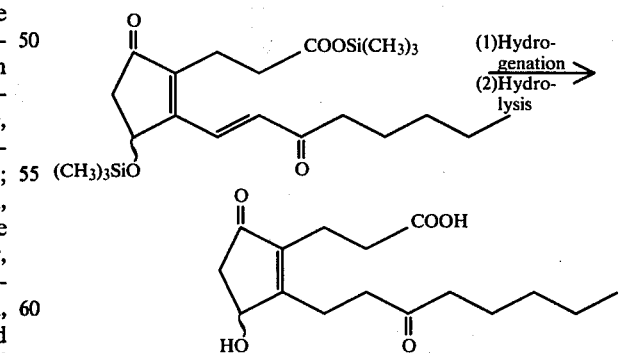

Preparation of Silyl derivative

3-[3-Hydroxy-5-oxo-2-(3-oxo-oct-1-enyl)cyclopent-1-enyl]propanoic acid (1.0 g.) was dissolved in dry, redistilled T.H.F. and treated with trimethylchlorosilane (0.75 ml.) and hexamethylenedisilazane (1.5 ml.). The solution was stirred with the rigorous exclusion of moisture. After 18 hours the solution was filtered in the absence of moisture and the filtrate evaporated to an oil; consisting of trimethylsilyl-3-[5-oxo-2-(3-oxo-oct-1-enyl)-3-trimethylsilyl oxy-cyclopent-1-enyl]propanoate.

Hydrogenation of Silyl derivative

Trimethylsilyl-3-[5-oxo-2-(3-oxo-oct-1-enyl)-3-trimethylsilyloxy-cyclopent-1-enyl]propanoate prepared above was dissolved in absolute ethanol (50 ml.) and hydrogenated over a 10% Pd/C catalyst (0.5 g.) at 50 p.s.i. for 2 hours. The catalyst was removed by filtration and the filtrate allowed to stand for 24 hours in the presence of an equal volume of water.

The product was removed after evaporation of the solvent and purified as outlined in the previous method. The product was 3-[3-hydroxy-5-oxo-2-(3-oxo-octan-1-yl)cyclopent-1-enyl]propanoic acid.

EXAMPLE 3

Hydrogenation of 3-[3-Hydroxy-5-oxo-2-(3-oxo-oct-1-enyl)cyclopent-1-enyl]propanoic acid 3-[3-Hydroxy-5-oxo-2-(3-oxo-oct-1-enyl)cyclopent-1-enyl]propanoic acid (3.0 g.) in ethanol (135 ml.) [containing 10% water] and triethylamine (15 ml.) was hydrogenated over a 10% Pd/C catalyst (1.2 g.) at 60 p.s.i. at room temperature for 1 hour.

The catalyst was removed by filtration and the filtrate rotary evaporated to give the crystalline triethylamine salt. The salt was dissolved in chloroform and shaken with 1 M hydrochloric acid. The organic phase was separated and shaken with sodium bicarbonate solution (×2). The aqueous phase was separated, washed with chloroform and then acidified with 1 M hydrochloric acid in the presence of fresh chloroform and shaken well. The organic layer was separated, washed with saturated brine, dried over anhydrous sodium sulphate and rotary evaporated to an oil.

Chromatography on a silicic acid (Bio Sil A) column with benzene containing increasing amounts of ethyl acetate separated a number of the stereoisomers of the main product, 3-[3-hydroxy-5-oxo-2-(3-oxo-octan-1-yl)cyclopentan-1-yl]propanoic acid.

15–20% ethyl acetate in benzene eluted one component indicated as the α-isomer.

25–30% ethyl acetate in benzene eluted another component designated as the β-isomer.

Further purification of these stereoisomers could be achieved if required by chromatography or in some cases by crystallisation.

α-Isomer

This isomer was purified by chromatography on a silicic acid column made up in benzene and increasing the polarity of the eluant slowly with ethylacetate. The product possessed no U.V. spectrum consistent with the absence of an extended chromophore. The mass spectrum exhibited a molecular ion at 384 units (methyl ester, trimethylsilylether derivative, m.wt. 384).

β-Isomer

Fractions obtained from the first column chromatography of the hydrogenation mixture containing the β-isomer on evaporation yielded an oil which deposited crystals on cooling at 0° C. Trituration of this material with cyclohexane and filtration yielded a white crystalline solid, m.p. 93.5° C.

Alternatively, the oil obtained may be re-chromatographed as above to yield a purer material from which the crystalline product may be isolated. This material had no U.V. spectrum and had a mass spectrum that was almost identical to that of the α-isomer.

Notable differences were however observed in their n.m.r. spectra and in their thin layer chromatography behaviour. Analysis supported the structure of the β-isomer ($C_{16}H_{26}O_5$).

Optically Active forms of the β-Isomer

Hydrogenation of the resolved starting materials (+) and (−) 3-[3-hydroxy-5-oxo-2-(3-oxo-oct-1-enyl)cyclopent-1-enyl]propanoic acid as above and applying the usual work-up the appropriately resolved stereoisomers were isolated. The crystalline β-isomer above was thus prepared in its (+) and (−) forms. The stereochemistry and enantiomeric nature of these forms was established in a number of ways:

(a) Melting points

The same m.p. (83°) for both enantiomers. Mixed m.p. between enantiomers slight depression (81°) however, on dissolution in a suitable solvent and isolation of crystalline material the m.p. was that of the racemate, i.e. 93°. Mixed m.p. between racemate and artificial racemate gave no depression.

(b) Optical Measurements

Equal and opposite optical rotations observed at equal concentrations in alcohol.

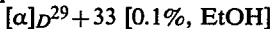
$[\alpha]_D^{29} + 33$ [0.1%, EtOH]

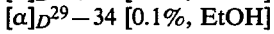
$[\alpha]_D^{29} - 34$ [0.1%, EtOH]

(c) Combined NMR and epimerisation studies

Epimerisation studies using sodium acetate in alcohol confirmed that the β-isomer possessed the natural prostaglandin configuration around the prostaglandin $C_8$ position. This fact, together with the NMR studies of the carbinolic proton at $C_{11}$, the shape and the position of the signal and the above optical measurements confirmed that the (−) β-isomer had the absolute configuration shown below:

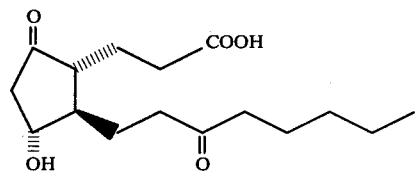

which thus corresponds with the structure of a known urinary metabolite of $PGE_2$. Its enantiomer however—the (+) β-isomer—is a novel compound as is the trans/trans racemate thereof.

EXAMPLE 4

Hydrogenation of 3-[3-Hydroxy-5-oxo-2-(7-carboxy-3-oxo-hept-1-enyl)-cyclopent-1-enyl]propanoic acid 3-[3-Hydroxy-5-oxo-2-(7-carboxy-3-oxo-hept-1-enyl)-cyclopent-1-enyl]propanoic acid (1.0 g.) was dissolved in absolute ethanol (150 ml.) containing triethylamine (15 ml.) and was hydrogenated over a 10% Pd/C catalyst (700 mg.) at 60 p.s.i., at R.T. for 1¼ hours. The catalyst was filtered off and the filtrate was rotary evaporated to a viscous oil. The oil was dissolved in water and acidified to pH 3 with oxalic acid solution and extracted with ethyl acetate (×3).

The organic extract was washed with sat. brine, dried over anhydrous magnesium sulphate and rotary evaporated to an oil which was chromatographed on a silicic acid column (Bio Sil A) made up in 2% methanol in chloroform. Many fractions were collected and examined by thin layer chromatography before rotary evaporation.

α-Isomer

This isomer was isolated as a viscous oil from the appropriate column fractions. On cooling and allowing to stand a crystalline solid was deposited. Trituration and recrystallisation gave material m.p. 102°–3° C. Characterisation of the solid showed this isomer possessed no U.V. spectrum and had a mass spectral molecular ion at 486 units (dimethyl ester, dimethoxime, trimethylsilyl ether derivative); Molecular Weight 486.

β-Isomer

This isomer was isolated as an oil and had very similar properties to the α-isomer. The thin layer chromatographic properties were different in a number of solvent systems.

γ-Isomer

This isomer was isolated on repeated purification of the α-isomer. The properties of this material paralleled the other isomers where thin layer chromatography in many systems again was markedly different.

Optically Active forms of the α-Isomer

Hydrogenation of the resolved compounds (+) and (−) 3-[3-hydroxy-5-oxo-2-(7-carboxy-3-oxo-hept-1-enyl)-cyclopent-1-enyl]propanoic acid according to the method described above afforded the mixture of resolved products. Using appropriate separation and purification techniques the (+) and (−) form of the α-isomer could be obtained.

The (+) and (−) forms on cooling and allowing to stand for 5–10 days deposited small amounts of a crystalline waxy solid. Complete crystallisation did not occur in contrast to the racemic material. On contact with small amounts of solvent the waxy solid dissolved.

| Optical Rotations | $[\alpha]_D$ (+) 9.0 (EtOH) $[\alpha]_D$ (−) 8.0 (EtOH) |
|---|---|

Other optical, physical and chemical measurements were able to support these structures such that the (−) α isomer had the absolute configuration shown below:

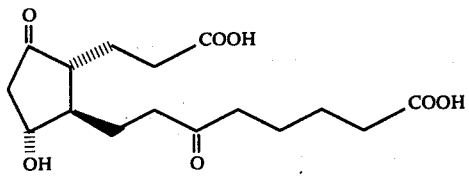

which thus corresponds with the structure of a known urinary metabolite of PGE$_2$. Its enantiomer however—the (+) α-isomer—is a novel compound as is the trans/trans racemate thereof.

EXAMPLE 5

Hydrogenation of Methyl-3-[3-hydroxy-5-oxo-2-(7-methoxycarbonyl-3-oxo-hept-1-enyl)-cyclopent-1-enyl]propanoate Methyl-3-[3-hydroxy-5-oxo-2-(7-methoxycarbonyl-3-oxo-hept-1-enyl)-cyclopent-1-enyl]propanoate (0.50 g.) was dissolved in absolute ethanol (50 ml.) containing triethylamine (2.5 ml.) and hydrogenated over a 10% Pd/C catalyst (250 mg.) for 1 hour at R.T. at 60 p.s.i.

The catalyst was removed by filtration and the filtrate was rotary evaporated to an oil which was chromatographed on a silicic acid column made up in 10% methylene chloride in chloroform. The hydrogenation mixture was separated into the types of structure seen in previous Example 4.

Further purification could be effected using further appropriate chromatographic procedures. The main product; methyl-3-[3-hydroxy-5-oxo-2-(7-methoxycarbonyl-3-oxo-heptan-1-yl)-cyclopentan-1-yl]propanoate possessed the expected physical data.

EXAMPLE 6

Hydrogenation of 3-[3-hydroxy-5-oxo-2-(3-oxo-oct-1-enyl)cyclopentan-1-yl]propanoic acid 3-[3-Hydroxy-5-oxo-2-(3-oxooct-1-enyl)cyclopentan-1-yl]propanoic acid (28 mg.) was dissolved in absolute alcohol (10 ml.) containing triethylamine (0.5 ml.) and hydrogenated over a 10% Pd/C catalyst (16 mg.) at R.T. at normal atmospheric pressure for 2 hours.

The catalyst was removed by filtration and the filtrate rotary evaporated to the triethylamine salt of the product, 3-[3-hydroxy-5-oxo-2-(3-oxo-octan-1-yl)cyclopentan-1-yl]propanoic acid. This material was dissolved in chloroform and extracted with sodium bicarbonate solution. The aqueous phase was washed with a little chloroform and acidified to pH 3-4 with citric acid solution. The acidified aqueous phase was shaken well with chloroform and allowed to separate. The organic phase was washed with a little sodium chloride solution, dried over anhydrous magnesium sulphate and rotary evaporated to a colourless oil. The spectroscopic data identified the oil as the previously prepared product, 3-[3-hydroxy-5-oxo-2-(3-oxo-octan-1-yl)cyclopentan-1-yl]propanoic acid.

This product was a mixture of stereoisomers which may be separated into their components.

EXAMPLE 7

Hydrogenation of 3-[3-Hydroxy-5-oxo-2-(3-oxo-octan-1-yl)cyclopent-1-enyl]propanoic acid

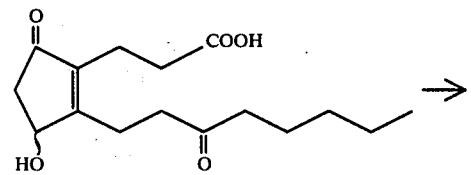

-continued

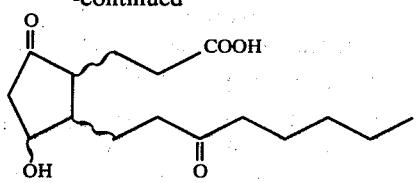

Using similar reaction conditions to those used in Example 3 there was obtained 3-[3-hydroxy-5-oxo-2-(3-oxooctan-1-yl)cyclopentan-1-yl]propanoic acid as a mixture of stereoisomers. Chromatographic techniques were used to generate separated isomers.

EXAMPLE 8

Preparation of 3-[3-hydroxy-5-oxo-2-(3-oxo-oct-1-enyl)cyclopentan-1-yl]propanoic acid 3-[2-Formyl-3-hydroxy-5-oxo-cyclopent-1-enyl]-propanoic acid (1.5 g.) was dissolved in absolute alcohol (160 ml.) and triethylamine (16 ml.) and hydrogenated over a 10% Pd/C catalyst (1.5 g.) at 60 p.s.i. at room temperature for 25 minutes.

The catalyst was removed by filtration and the filtrate rotary evaporated to an oil. The oil consisted of 3-[2-formyl-3-hydroxy-5-oxo cyclopentan-1-yl]propanoic acid.

The purified oil product was dissolved in redistilled dry T.H.F. (30 ml.) and treated with excess n-hexanoyl methylene triphenylphosphorane (prepared from triphenyl-2-oxoheptyl phosphonium bromide, 6.0 g.) in dry T.H.F. (30 ml.) in dropwise additions at R.T. under dry $N_2$. The reaction mixture was heated for 18 hours at 60°-70° C.

The solution after this time was rotary evaporated to an oil which was dissolved in chloroform and shaken with excess sodium bicarbonate solution. The organic phase was separated and washed with a further amount of bicarbonate solution. The aqueous phases were then combined, acidified with citric acid to pH 4, and shaken well with chloroform. The $CHCl_3$ layer was separated and shaken with sat. brine, dried over anhydrous magnesium sulphate and rotary evaporated to an oil.

The oil was chromatographed on a silicic acid column (Bio Sil A) made up in ethylacetate/toluene (3:7). Elution with the same solvent combination gave a number of fractions which included separated stereoisomers of the compound. 3-[3-hydroxy-5-oxo-2-(3-oxooct-1-enyl)cyclopentan-1-yl]propanoic acid. The U.V. spectrum showed absorption at 230 n.m. and the mass spectrum gave a molecular ion at 382 units. (Methylester, trimethylsilyl ether derivative). (Molecular Weight 382).

We claim:

1. Racemate or mixture of racemates of the formula:

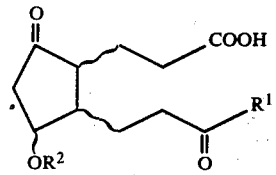

wherein $R^2$ is hydrogen; acetyl, or trimethylsilyl, and $R^1$ is a straight or branched $C_{1-8}$ alkyl group substituted by a COOH group; and $C_{1-4}$ alkyl esters thereof.

2. The compound of claim 1, which is 3-[3-hydroxy-5-oxo-2-(7-carboxy-3-oxoheptan-1-yl)cyclopentan-1-yl]propionic acid.

3. Compound of the formula

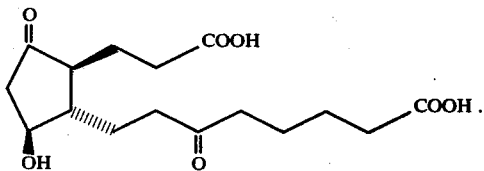

4. Racemate of

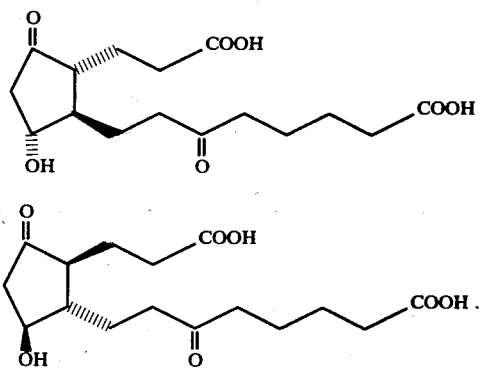

and

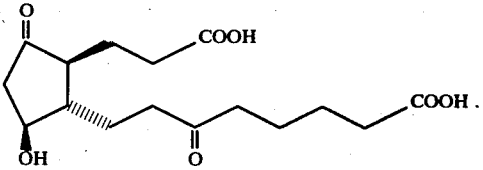

* * * * *

UNITED STATES PATENT OFFICE
CERTIFICATE OF CORRECTION

Patent No. 4,151,199                Dated April 24, 1979

Inventor(s) William Dawson, et al.

It is certified that error appears in the above-identified patent and that said Letters Patent are hereby corrected as shown below:

On the front page, there should be an additional entry in Column 1, as follows:

--[30]  Foreign Application Priority Data
   Dec. 9, 1974 [GB] United Kingdom...........53224/74--.

Signed and Sealed this

Fourth Day of December 1979

[SEAL]

Attest:

SIDNEY A. DIAMOND

Attesting Officer      Commissioner of Patents and Trademarks